(12) United States Patent
Irion

(10) Patent No.: US 9,717,398 B2
(45) Date of Patent: Aug. 1, 2017

(54) LIGHTING SYSTEM FOR ENDOSCOPIC EXAMINATIONS

(75) Inventor: Klaus M. Irion, Emmingen-Liptingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1577 days.

(21) Appl. No.: 11/524,681

(22) Filed: Sep. 21, 2006

(65) Prior Publication Data

US 2007/0073109 A1 Mar. 29, 2007

(30) Foreign Application Priority Data

Sep. 23, 2005 (DE) .................. 10 2005 045 729

(51) Int. Cl.
*A61B 1/06* (2006.01)
*A61B 1/005* (2006.01)

(52) U.S. Cl.
CPC .......... *A61B 1/0051* (2013.01); *A61B 1/0615* (2013.01); *A61B 1/0676* (2013.01); *A61B 1/0684* (2013.01)

(58) Field of Classification Search
CPC .......... A61B 1/07; A61B 1/00149; A61B 1/06; A61B 1/0615; A61B 1/0623; A61B 1/0676; A61B 1/0684
USPC ......... 362/572–574; 600/129, 164, 109–111, 600/113, 166–179; 348/65–73
See application file for complete search history.

(56) References Cited

U.S. PATENT DOCUMENTS

| | | | | |
|---|---|---|---|---|
| 4,491,865 A | * | 1/1985 | Danna et al. | 348/71 |
| 5,166,787 A | * | 11/1992 | Irion | 348/75 |
| 5,547,455 A | * | 8/1996 | McKenna et al. | 600/113 |
| 6,007,484 A | * | 12/1999 | Thompson | 600/173 |
| 6,066,090 A | * | 5/2000 | Yoon | A61B 1/00045 600/113 |
| 6,331,156 B1 | * | 12/2001 | Haefele et al. | 600/179 |
| 6,398,725 B1 | * | 6/2002 | Thompson | 600/173 |
| 6,450,950 B2 | | 9/2002 | Irion | |
| 6,488,619 B1 | * | 12/2002 | Miyanaga | 600/179 |
| 6,492,725 B1 | * | 12/2002 | Loh et al. | 257/723 |

(Continued)

FOREIGN PATENT DOCUMENTS

| | | |
|---|---|---|
| DE | 100 61 107 | 6/2002 |
| EP | 1 685 791 | 8/2006 |
| WO | WO 2006/037034 | 4/2006 |

OTHER PUBLICATIONS

European Search Report, Feb. 7, 2007, 6 pages.
German Search Report, Jun. 1, 2006, 4 pages.

*Primary Examiner* — Alexandra Newton
(74) *Attorney, Agent, or Firm* — Whitmyer IP Group LLC

(57) ABSTRACT

The invention relates to a lighting system for endoscopic examinations having a lighting unit that includes at least two LED elements for illuminating an area of examination that is to be observed by means of an endoscope optic. To create a lighting system for endoscopic examinations that ensures a constantly sufficient illumination of the area of examination, it is proposed according to the invention that the direction of radiation of the lighting unit can be displaced between a direction essentially perpendicular to the direction of observation of the endoscope optic upon insertion into the area of examination and a direction essentially in the direction of observation of the endoscope optic after insertion into the area of examination.

13 Claims, 7 Drawing Sheets

(56) References Cited

U.S. PATENT DOCUMENTS

| | | | |
|---|---|---|---|
| 6,648,816 B2* | 11/2003 | Irion et al. | 600/173 |
| 7,270,439 B2* | 9/2007 | Horrell et al. | 362/119 |
| 2003/0191364 A1 | 10/2003 | Czarnek et al. | |
| 2004/0249247 A1* | 12/2004 | Iddan | 600/170 |
| 2005/0049462 A1 | 3/2005 | Kanazawa | |
| 2005/0096502 A1* | 5/2005 | Khalili | 600/106 |
| 2005/0099810 A1* | 5/2005 | Tasson et al. | 362/250 |
| 2005/0234296 A1* | 10/2005 | Saadat | A61B 1/0008 600/129 |
| 2005/0288555 A1* | 12/2005 | Binmoeller | 600/160 |
| 2006/0069313 A1* | 3/2006 | Couvillon | 600/178 |
| 2006/0069314 A1* | 3/2006 | Farr | 600/179 |
| 2006/0155168 A1* | 7/2006 | Pease | 600/131 |
| 2007/0002582 A1* | 1/2007 | Burwell et al. | 362/572 |

* cited by examiner

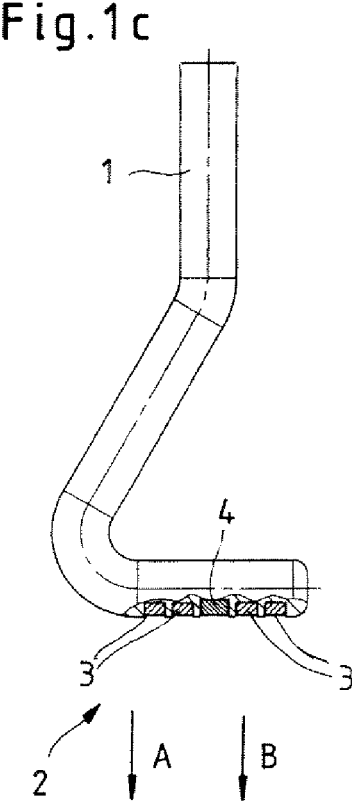

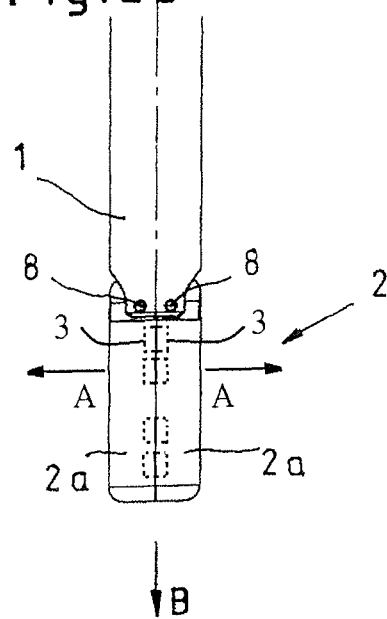
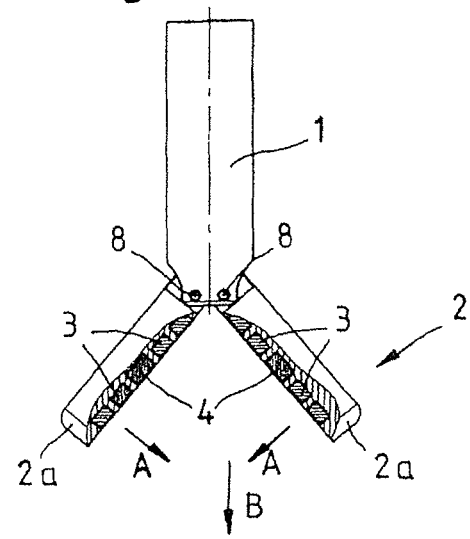
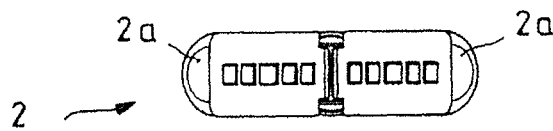

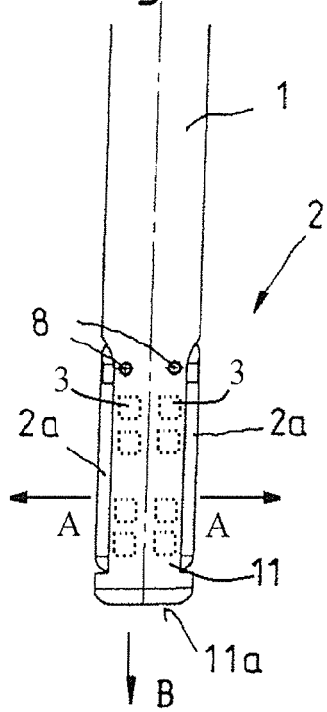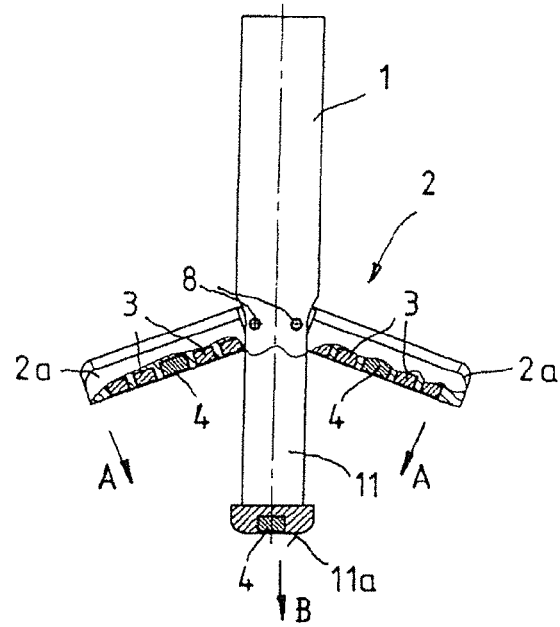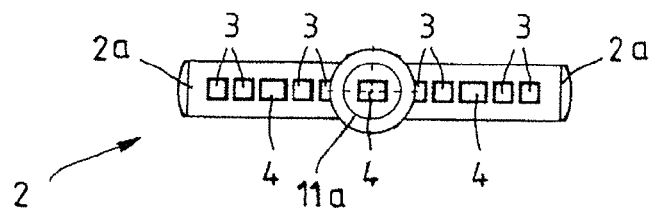

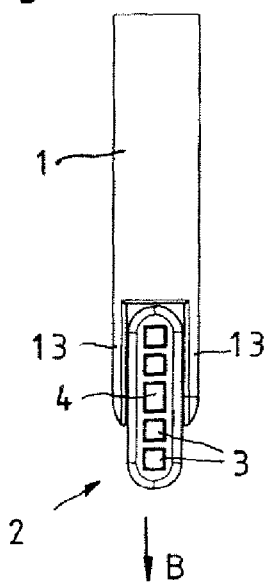
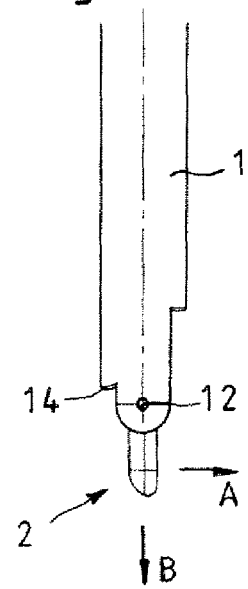
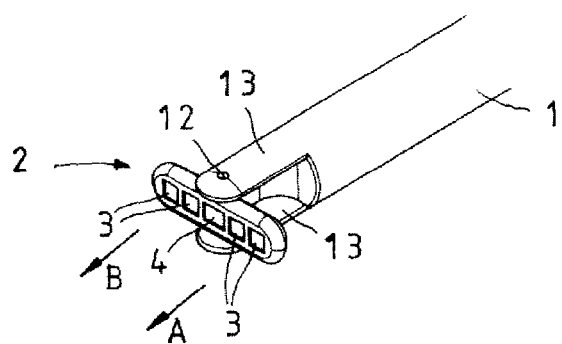

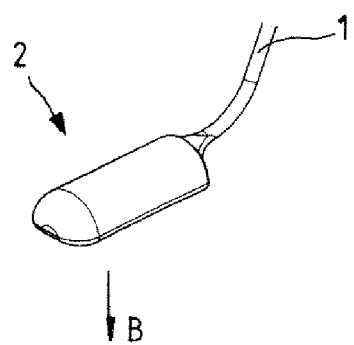
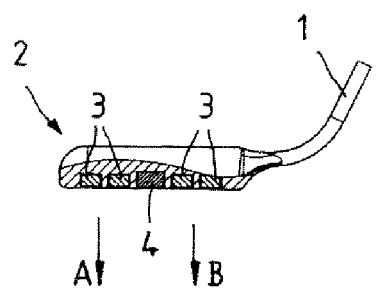

LIGHTING SYSTEM FOR ENDOSCOPIC EXAMINATIONS

CROSS-REFERENCE TO RELATED APPLICATIONS

The present application claims priority of German patent application No. 10 2005 045 729.0 filed on Sep. 23, 2005, the content of which is incorporated herein by reference.

FIELD OF THE INVENTION

The invention relates to a lighting system for endoscopic examinations having a lighting unit with at least two LED elements for illuminating an examination area that is to be examined by an endoscope optic.

BACKGROUND OF THE INVENTION

The use of endoscopes has successfully proven itself in surgery for many years, and serves in many cases as a minimally invasive alternative procedure to the conventional open surgery. To be able to examine the area of application and to operate there by means of the endoscope optic, which can take the classic form for instance of a relay lens system, a fiber image conductor, or else as an electronic image sensor chip (CMOS, CCD) for video image photography, it is absolutely essential to illuminate the area of examination as well as possible. Besides their use in human and veterinary medicine, endoscopic examinations have also proven effective in technical areas, for instance for examining hollow cavities. Even in these application areas, good illumination of the area of examination is indispensable for good imaging by the endoscope optic.

The illumination of an area of investigation is normally provided by a light conductor, consisting of fiberglass clusters, by which light from an external light source is conducted into the area of examination. Because this lighting system, for instance for purposes of cooling and wiring, is technically very complex, it has been a familiar practice in the art for some time to use lighting systems that are provided with LED elements and are affixed on the distal end of the endoscope shaft. The advantage of these LED lighting systems mounted on the distal end is that they avoid coupling losses in the light conductors and the LED elements have a long useful life.

The use of a lighting unit that includes a lighting system for endoscopic examinations with an LED element is, for instance, known from DE 100 61 107 A1. The disadvantage of the known lighting systems, however, is the low effective density that is to be produced associated with the LED elements, so that even with special arrangements of the LED elements on the distal front end of the endoscope shaft, it is only possible to produce an illumination of the area of examination that is not sufficient for all cases of application.

Consequently it is the object of the invention to create a lighting system for endoscopic examinations of the aforementioned type, which ensures a constantly sufficient illumination of the area of examination.

SUMMARY OF THE INVENTION

This object is fulfilled according to the invention in a manner characterized in that the LED elements of the lighting unit are arranged in such a way that the radiation direction of the lighting unit can be moved between a direction essentially perpendicular to the direction of observation of the endoscope optic upon its insertion into the area of examination, and a direction essentially in the direction of observation of the endoscope optic after insertion into the area of examination.

Because of the displacement of the LED elements, according to the invention, in a direction essentially perpendicular to the direction of observation of the endoscope optic upon insertion into the area of examination, it is possible for the first time, in the use of LED elements for illuminating an endoscopic area of examination, not to be required to position the LED elements on the distal front surface of the endoscope and thus on an extremely restricted surface area. Displacing the lighting unit after insertion into the area of examination makes possible thereafter the sufficient illumination by means of the LED elements that now are illuminating in the direction of observation of the endoscope optic.

According to a preferred embodiment of the invention, it is proposed that the LED elements of the lighting unit are arranged in a row. This arrangement of the LED elements in a row allows a flat and superimposed illumination of the area of examination from diverse angles of incidence, leading to improved depth perception.

According to a practical embodiment of the invention, the lighting unit is positioned away from the distal front surface on the distal end of an endoscope shaft and thus in immediate vicinity of the endoscope optic. Alternatively, a lighting system can be configured according to the invention but as an autonomous instrument, which is introduced into the area of examination in addition to an endoscope optic.

It is further proposed with the invention that, to improve the illumination of the area of examination, the lighting unit should consist of several lighting subunits that are equipped with LED elements and advantageously can be rotated with respect to one another on the endoscope shaft. By using several lighting subunits, each of which is equipped with LED elements, the total number of the LED elements available for illumination can be clearly increased. In addition, because of the mutual rotatability of the individual lighting subunits with respect to one another, diverse angles of incidence of the light can be produced.

According to a preferred embodiment of the invention, the individual lighting units are arranged symmetrically to one another with respect to the longitudinal axis of the endoscope optic. It is also possible to have preferably two or even more lighting units present, which advantageously are arranged symmetrically to one another with respect to the longitudinal axis of the endoscope optic and thus constitute circle segments in cross-section (perpendicular to the longitudinal axis of the endoscope optic).

To ensure a uniform illumination of the area of examination, the LED elements of the lighting unit or of the lighting subunits are, according to the invention, preferably arranged symmetrically to one another with respect to the endoscope optic.

According to a first practical embodiment of the invention having a lighting system mounted on the distal end of an endocope shaft, it is proposed that the endoscope optic should be positioned in the area of the rotatable mounting of the lighting subunits on the endoscope shaft, so that the endoscope optic is positioned basically in a plane with the lighting subunits of the lighting system.

With an alternative embodiment of the invention it is proposed that the endoscope optic configures the distal end of the endoscope shaft, while the lighting unit is positioned proximally displaced behind the endoscope optic.

To divert the heat produced by the LED elements of the lighting unit, it is further proposed with the invention that a heat-diverting system, in particular in the form of an electric conductor, should be positioned in the endoscope shaft.

It is finally proposed with the invention that the endoscope optic should be coupled with an imaging system, which can capture tissue fluorescent images after the disconnection of the LED elements of the lighting unit. This time-dissolved fluorescence imaging is particularly possible in the use of blue luminescent LED elements, which irradiate blue luminescence at a wavelength of approximately 405 nm and stimulate the tissue to a xeno- or auto-fluorescence.

Additional characteristics and advantages of the invention can be seen from the appended illustrations, in which six embodiments of a lighting system for endoscopic examinations according to the invention are depicted in exemplary manner.

BRIEF DESCRIPTION OF THE DRAWINGS

FIG. 1b shows an enlarged and partially cutout view of detail IB of FIG. 1a.

FIG. 1c shows a side view of the lighting system of FIG. 1a in inserted position.

FIG. 2a shows a side view of a second embodiment of a lighting system according to the invention in the insertion position.

FIG. 2b shows a partly cutout view of the depiction in FIG. 2a in the inserted position.

FIG. 2c shows a view from below of the depiction in FIG. 2b.

FIG. 4a shows a side view of a fourth embodiment of a lighting system according to the invention, in the insertion position.

FIG. 4b shows a partly cutout view of the depiction in FIG. 4a in inserted position.

FIG. 4c shows a view from below of the depiction in FIG. 4b.

FIG. 5a shows a side view of a fifth embodiment of a lighting system according to the invention in the insertion position.

FIG. 5b shows a side view, at a 90 degree angle, of the depiction in FIG. 5a.

FIG. 5c shows a perspective view of the depiction in FIGS. 5a and 5b in the inserted position.

FIG. 6a shows a perspective view of a sixth embodiment of a lighting system according to the invention in the inserted position.

FIG. 6b shows a partly cut-out side view of the depiction in FIG. 6a.

DETAILED DESCRIPTION OF THE INVENTION

Figure 1A:
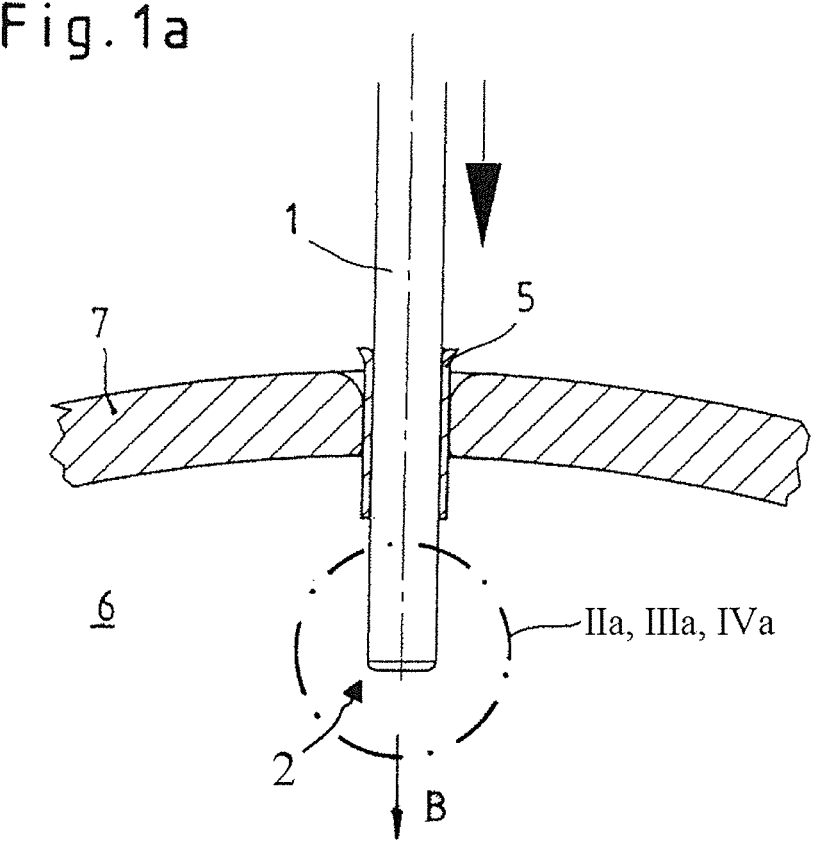
FIG. 1a shows a side view of a first embodiment of a lighting system according to the invention upon insertion into the area of examination.

The lighting systems illustrated in FIGS. 1a to 6b serve to illuminate endoscopic areas of examination, independently of whether they are used in medical or technical endoscopy.

In the illustrated embodiments the lighting systems consist of a lighting unit 2 that is positioned on the distal end of an endoscope shaft 1 and in turn includes at least two LED elements 3. For observing the area of examination that is illuminated by means of the lighting unit 2, on the distal end of the endoscope shaft an endoscope optic 4 is further positioned which can take the classical form of a relay lens system or can be a CCD or CMOS image sensor for video photography.

All illustrated lighting systems have the peculiarity that the lighting unit 2 is positioned, not on the distal front surface of the endoscope shaft but laterally on the distal end area of the endoscope shaft 1, so that the arrangement of the LED elements 3 is not restricted to the small front surface.

As is explained hereafter in greater detail with reference to the various embodiments for configuring the lighting system, the LED elements 3 of the lighting units 2 are arranged on the endoscope shafts 1 in such a way that the direction of radiation of the lighting units 2 can be displaced between a direction essentially perpendicular to the direction of observation of the endoscope optic 4 upon insertion into the area of examination and a direction essentially in the direction of observation B of the endoscope optic 4, after insertion into the area of examination.

FIG. 1a shows the insertion of an endoscope shaft 1 by means of a trocar sleeve 5 into an area of examination, for instance a patient's abdominal cavity 6. For this purpose the endoscope shaft 1 is inserted into the abdominal area 6 in the illustrated longitudinal straight position by means of the trocar sleeve 5 positioned in the abdominal wall 7. This straight insertion direction corresponds to the actual direction of observation B of the endoscope optic 4.

Figure 1B:
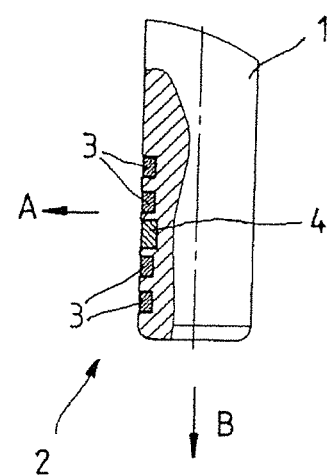

As can be seen from the sectional depiction in FIG. 1b of the distal end of the endoscope shaft 1 of FIG. 1a, the lighting unit 2 consisting of four LED elements 3 is positioned outside the distal front surface on the endoscope shaft 1 in such a way that the direction of radiation A of the LED elements 3 of the lighting unit 2, upon insertion, points in a direction which is essentially perpendicular to the direction of observation B of the endoscope optic 4, which this optic assumes in observing the area of examination.

As can further be seen from FIG. 1b, the illustrated lighting unit 2 is constructed in such a way that the LED elements 3 are arranged symmetrically to one another with respect to the endoscope optic 4 configured as an opto-electronic image sensor.

In order to observe and examine the area of examination, at least the distal area of the endoscope shaft 1 that contains the lighting unit 2, after insertion into the area of examination, can be rotated into the position shown in FIG. 1c, in which the direction of radiation A of the LED elements 3 of the lighting unit 2 corresponds essentially to the direction of observation B of the endoscope optic 4. Because of the symmetrical arrangement of the LED elements 3 in a row around the endoscope optic 4, as can be seen in FIG. 1c, it is possible to produce a much larger density capacity for illuminating the area of examination than is possible with the arrangement of the LED elements 3, as known in the art, on the small distal front surface of the endoscope shaft 1.

The embodiments of lighting systems for endoscopic examinations shown in FIGS. 2a through 4c are distinguished from the previously described configurations according to FIGS. 1a through 1c in that the lighting units 2 of the three illustrated alternative forms of construction each consist of two lighting subunits 2a, which are positioned to rotate around guide points 8 with respect to one another on the endoscope shaft 1. Alternatively it is also possible, however, to provide three, four, or more lighting subunits.

In the second embodiment seen in FIGS. 2a through 2c, the distal area of the endoscope shaft 1 is configured as divided in the axial direction of the endoscope shaft 1 for configuring the two lighting subunits 2a. The two lighting subunits 2a, which can each rotate by one guide point 8, each have four LED elements 3 as well as an endoscope optic 4 configured as an opto-electronic image sensor, such that the LED elements 3 in turn are arranged symmetrically around the endoscope optic in order to ensure a uniform illumination of the area of examination.

In this embodiment, in which several distal endoscope optics 4 are used, which are connected by light-conducting fibers with an imaging device (screen), either several individual images are shown each from other viewing perspectives, so that possibly only individual images can be shown, even by switching, or else a stereo view is made up of two or more individual images. The latter alternative produces images with a very good three-dimensional or depth effect.

FIG. 2a shows the extended straight insertion position of the endoscope shaft 1, in which the flat surfaces of the two lighting subunits 2a, equipped with the LED elements 3 and the endoscope optics 4, are closed and firmly contiguous to one another and form an essentially flush distal extension of the endoscope shaft 1.

For superimposition into the examination positions indicated in FIGS. 2b and 2c, the lighting subunits 2a are rotated around the guide points 8, for instance by an actuation element mounted in the endoscope shaft 1, in particular a push-pull rod or a Bowden cable, until the direction of radiation A of the LED elements 3 of the lighting subunits 2a essentially corresponds to the direction of observation B of the endoscope optic 4. FIG. 2b shows a transitional position that can be used for examination purposes, in which the LED elements 3 illuminate the area of examination from diverse angles of inclination.

Figure 3A:
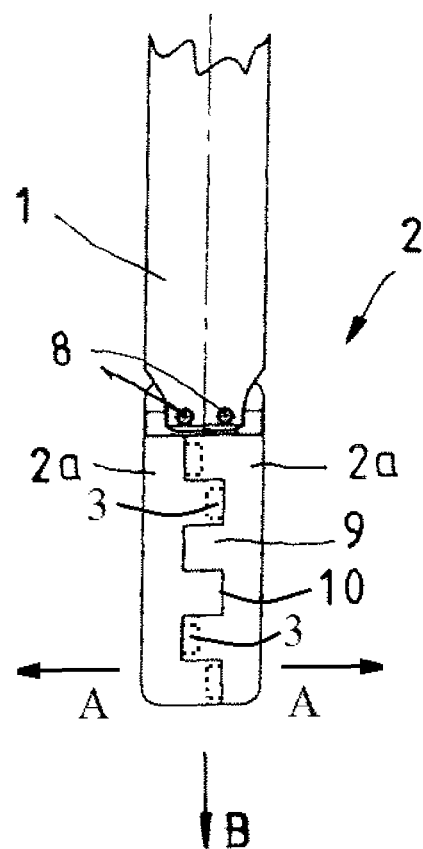
FIG. 3a shows a side view of a third embodiment of a lighting system according to the invention in the insertion position.
Figure 3B:
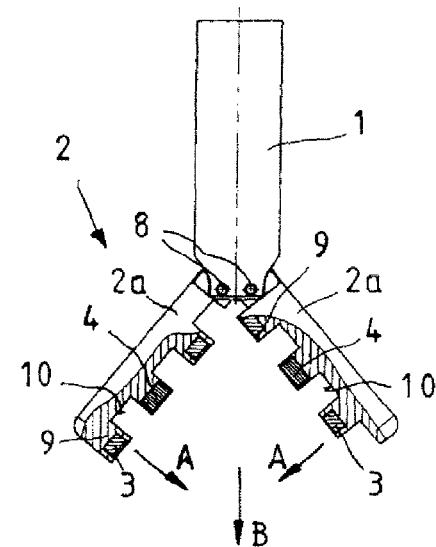
FIG. 3b shows a partly cutout view of the depiction in FIG. 3a in inserted position.
Figure 3C:
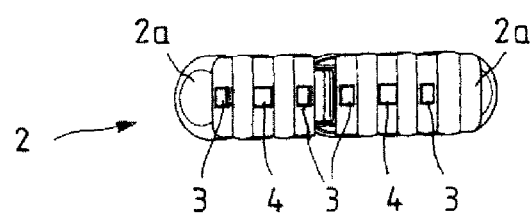
FIG. 3c shows a view from below of the depiction according to FIG. 3b.

The third embodiment, shown in FIGS. 3a to 3c, is distinguished from the previously described embodiment shown in FIGS. 2a through 2c in that the surfaces of the two lighting subunits 2a equipped with the LED elements 3 and endoscope optics 4 are not flat in form but rather comb-like with protuberances 9 and indentations 10. As can be seen in FIG. 3a, the protuberances 9 and indentations 10 of the two lighting subunits 2a are arranged here so that, in the insertion position of the endoscope shaft, they engage with one another in form-locking position and the two lighting subunits 2a in turn form an essentially flush distal extension of the endoscope shaft 1.

The LED elements 3 and the opto-electronic image sensors of the endoscope optics 4 in this embodiment are each positioned on the free ends of the protuberances 9, such that the illustrated embodiment for each lighting subunit 2a includes two LED elements 3 as well as an endoscope optic 4 that is centered between the LED elements 3 and takes the form of an opto-electronic image sensor.

Alternatively to the embodiments illustrated in FIGS. 2a through 3c, in which the opto-electronic image sensors of the endoscope optics 4 are positioned only on the lighting subunits 2a, it is also possible of course to position at least one opto-electronic image sensor as sole, or additional endoscope optic 4 in the area of the rotatable positioning of the lighting subunits 2a on the guide points 8.

FIGS. 4a through 4c show an additional embodiment, in which the lighting unit 2 again consists of two lighting subunits 2a that can rotate with respect to one another around guide points 8. In this embodiment the distal end of the endoscope shaft 1 is configured by a bridge-shaped web, which spans the two lighting subunits 2a in the insertion position shown in FIG. 4a.

As can be seen in particular from FIG. 4b, the two lighting subunits 2a are positioned on the guide points 8 so that they can unfold laterally out of the web 11. The two rotatable lighting subunits 2a in this embodiment each have four LED elements 3 as well as one endoscope optic 4 configured as opto-electronic image sensor, such that the LED elements 3 again are arranged symmetrically around the endoscope optic 4 in order to ensure a uniform illumination of the area of examination.

In addition, in this embodiment another opto-electronic image sensor serving as endoscope optic 4 is positioned on a distal front surface 11a of the web 11.

In the straight insertion position shown in FIG. 4a, the front surface 11a of the web 11 extends beyond the lighting subunits 2a into the unfolding direction of the lighting subunits 2a in such a way that the front surface 11a of the web 11 extends the endoscope shaft essentially flush on the outer surfaces of the two lighting subunits 2a.

In the fifth embodiment, shown in FIGS. 5a through 5c, the one-part lighting unit 2 is positioned so that it can rotate around a pivot axis 12 on the distal end of the endoscope shaft. The distal end of the endoscope shaft 1 is configured with two arms 13 for this purpose, in such a way that the lighting unit 2 is positioned so that it can rotate around the pivot axis 12 between the two distal arms of the endoscope shaft 1.

In the insertion position illustrated in FIGS. 5a and 5b, the lighting unit 2 is rotated in such a way that it is directed in the axial direction of the endoscope shaft 1 and thus can be inserted into the area of examination with the endoscope shaft in straight position.

In the position inserted into the area of examination, the lighting unit 2, as can be seen from FIG. 5c, is rotated by 90 degrees until it is situated perpendicular to the axial direction of the endoscope shaft 1. A stop 14 configured on the endoscope shaft 1 restricts, on the one hand, the angle of rotation of the lighting unit 12 and, in addition, allows only a rotation in a direction around the pivot axis 12.

As can also be seen from FIGS. 5a and 5c, the lighting unit 2 in this embodiment includes four LED elements 3 as well as an endoscope optic 4 configured as an opto-electronic image sensor, such that the LED elements 3 again are positioned symmetrically around the endoscope optic 4 in order to ensure a uniform illumination of the area of examination.

Alternatively to the embodiment depicted in FIGS. 5a through 5c, similar configurations can be realized in which, on the proximal end from the lighting unit 2 that can rotate by 90 degrees, one or more additional lighting units 2 are positioned so that they can rotate around pivot axes 12 in the endoscope shaft 1, and these additional lighting units 2 then, as a rule, are each equipped only with LED elements 3 to illuminate the area of examination and are positioned at an 180 degree angle to one another in the endoscope shaft 1. To be able to examine the area of examination also by a stereo view, it is necessary to equip at least one of the additional lighting units 2 additionally with an endoscope optic 4.

In the sixth embodiment of a lighting system, illustrated in FIGS. 6a and 6b, the lighting unit 2, similarly as in the depiction of FIGS. 1a through 1c, forms the distal end of the endoscope shaft 1, which in this case however is configured as a mere conductor for the supply of the LED elements 3 and of the endoscope optic 4. In this embodiment as well, the lighting unit 2 includes four LED elements 3 as well as an endoscope optic 4 configured as an opto-electronic image sensor, such that the LED elements 3 again are positioned symmetrically around the endoscope optic 4.

In the insertion position, not illustrated, the lighting unit 2 forms the extended straight extension of the endoscope shaft 1. The lighting unit 2 then is at an angle with respect to the endoscope shaft 1 only in the area of examination, as this is shown in FIGS. 6a and 6b.

As previously illustrated and described, all lighting systems have the peculiarity that the lighting units 2 are not positioned on the distal front surface of the endoscope shaft 1, but instead laterally on the distal end area of the endoscope shaft 1, so that the arrangement of the LED elements 3 is not restricted to the small front surface. For this purpose the LED elements 3 of the lighting units 2 are arranged on the endoscope shafts 1 in such a way that the direction of radiation of the lighting units 2 can be displaced between a direction essentially perpendicular to the direction of observation of the endoscope optic 4 upon insertion into the area of examination and a direction essentially in the direction of observation B of the endoscope optic 4 after insertion into the area of examination.

For configuring the LED elements 3, preference is given to using LED elements 3, which for instance radiate blue light at a wavelength of about 405 nm and stimulate the tissue to a xeno- or auto-fluorescence. The endoscope optic 4 in this embodiment of the time-dissolved fluorescence imaging is advantageously coupled with an imaging system that can record tissue fluorescence images after disconnection of the LED elements 3 of the lighting unit 2.

The advantage of the LED illumination to intracorporal fluorescence stimulation consists in the fact that the LEDs 3, contrary to the short-wave lamps or mechanically shuttered constant lamps, can be switched with great precision. Thus, after a constant fluorescence stimulation, it is possible to disconnect and switch over to fluorescence stimulation ("fluorescence lifetime imaging"). In addition periodic stimulation can be performed precisely and thereafter the fluorescence can be produced periodically.

What is claimed is:

1. An endoscope shaft with a lighting system for endoscopic examinations comprising:
    at least two lighting subunits configured at a distal end of the endoscope shaft, the lighting subunits each having a proximal end which is mounted to the endoscope shaft with a pivot pin, the pivot pins of the lighting subunits providing different pivot axes around which the lighting subunits are pivotable relative to each other,
    each lighting subunit having a body with at least two LED elements and an endoscope optic, the LED elements and the endoscope optic being positioned on a surface of the body other than a distal front surface,
    the lighting subunits being pivotable between a closed configuration and an open configuration,
    wherein in the closed configuration, each lighting subunit extends from the endoscope shaft in parallel with a longitudinal axis of the distal end of the endoscope shaft, and the LED elements of the lighting subunits each point in a direction that is perpendicular to the longitudinal axis, and
    wherein in the open configuration, each lighting subunit extends non-parallel to the longitudinal axis, and the LED elements of the lighting subunits each point in a direction that is non-perpendicular to the longitudinal axis.

2. The endoscope shaft according to claim 1, wherein the LED elements of the lighting subunits are arranged in rows.

3. The endoscope shaft according to claim 1, wherein an endoscope optic is positioned on the endoscope shaft in an area of the pivotable mounting of the lighting subunits.

4. The endoscope shaft according to claim 1, wherein an endoscope optic forms the distal end of the endoscope shaft.

5. The endoscope shaft according to claim 1, wherein a heat diverting system is positioned in the endoscope shaft.

6. The endoscope shaft according to claim 5, wherein the heat diverting system comprises an electric conductor.

7. The endoscope shaft according to claim 1, wherein the LED elements radiate light in the blue light range.

8. The endoscope shaft according to claim 7, wherein the LED elements radiate light at about 405 nm.

9. The endoscope shaft according to claim 1, wherein the LED elements are configured to provide constant or periodic fluorescent stimulation of tissue.

10. The endoscope shaft according to claim 1, wherein the endoscope optics of the lighting subunits are coupled with an imaging system, which is configured to capture tissue fluorescence images after disconnection of the LED elements of the lighting subunits.

11. The endoscope shaft according to claim 1, wherein for each lighting subunit, the LED elements and the endoscope optic are positioned in a row.

12. The endoscope shaft according to claim 1, wherein for each lighting subunit, the LED elements are positioned symmetrically relative to the endoscope optic.

13. The endoscope shaft according to claim 1, wherein the at least two lighting subunits are configured to be mutually pivotable relative to each other.

* * * * *